United States Patent [19]

Buchecker et al.

[11] Patent Number: 5,399,292
[45] Date of Patent: Mar. 21, 1995

[54] FLUORO-SUBSTITUTED PHENYL-CYCLOHEXYLACETYLENES

[75] Inventors: Richard Buchecker, Zurich; Martin Schadt, Seltisberg, both of Switzerland

[73] Assignee: Hoffmann-La Roche Inc., Nutley, N.J.

[21] Appl. No.: 236,868

[22] Filed: May 2, 1994

Related U.S. Application Data

[63] Continuation of Ser. No. 131,268, Oct. 1, 1993, abandoned.

[30] Foreign Application Priority Data

Oct. 23, 1992 [CH] Switzerland .................. 3309/92
Nov. 3, 1992 [CH] Switzerland .................. 3425/92
Mar. 16, 1993 [CH] Switzerland .................. 789/93

[51] Int. Cl.[6] .................. C09K 19/30; C09K 19/34; C07D 239/02; C07C 43/02; C07C 25/13
[52] U.S. Cl. .................. 252/299.63; 252/299.61; 252/299.66; 544/303; 544/334; 546/345; 549/380; 570/127; 568/656; 359/103
[58] Field of Search .................. 252/299.01, 299.61, 252/299.63, 299.66, 299.67; 359/103; 544/303, 334; 546/345; 549/380; 568/656; 570/127

[56] References Cited

U.S. PATENT DOCUMENTS

| | | | |
|---|---|---|---|
| 4,565,425 | 1/1986 | Petrzilka et al. | 252/299.5 |
| 4,676,604 | 6/1987 | Petrzilka | 252/299.5 |
| 4,816,180 | 3/1989 | Goto et al. | 252/299.63 |
| 5,013,478 | 5/1991 | Petrzilka | 252/299.63 |
| 5,242,618 | 9/1993 | Krause et al. | 252/299.6 |

FOREIGN PATENT DOCUMENTS

| | | |
|---|---|---|
| 3807682 | 3/1988 | Germany . |
| 4000535 | 6/1991 | Germany . |
| 4105742 | 8/1992 | Germany . |
| 88/07523 | 10/1988 | WIPO . |

OTHER PUBLICATIONS

Abstract No. 88-279450/40 for DE 3 807 682-A.
Petrzilka, M., and A. Germann, *Mol. Cryst. Liq. Cryst.*, vol. 131, pp. 327-342 (1985).
Pugh, C., and V. Percey, *Mol. Cryst. Liq. Cryst.*, vol. 178, pp. 193-217 (1990).

*Primary Examiner*—Shean Wu
*Attorney, Agent, or Firm*—George M. Gould; George W. Johnston; John P. Parise

[57] ABSTRACT

Fluoro-substituted phenyl-cyclohexylacetylenes have the formula:

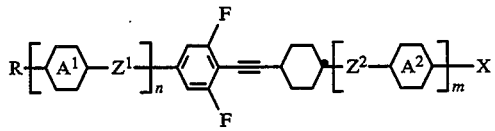

wherein
R signifies alkyl, alkoxy, alkenyl or alkenyloxy with 1 or, respectively, 2 to 12 carbon atoms in which one $CH_2$ group can be replaced by oxygen and/or one or more hydrogen atoms can be replaced by fluorine atoms, with the proviso that two oxygen atoms are not directly adjacent;
$A^1$ represents 1,4-phenylene, pyridine-2,5-diyl, pyrimidine-2,5-diyl, trans-1,4-cyclohexylene or trans-1,3-dioxane-2,5-diyl;
$A^2$ signifies trans-1,4-cyclohexylene or 1,4-phenylene which is optionally substituted with fluorine;
$Z^1$ signifies a single covalent bond, $-CH_2CH_2-$, $-OCH_2-$, $-CH_2O-$, $-(CH_2)_4-$, $-O(CH_2)_3-$, $-(CH_2)_3O-$ or, when ring $A^1$ represents a saturated ring, also the trans form of $-CH=CH(CH_2)_2-$ or $-CH=CHCH_2O-$;
$Z^2$ signifies a single covalent bond, $-CH_2-CH_2-$, $-OCH_2-$, $-CH_2O-$, $-(CH_2)_4-$, $-O(CH_2)_3-$, $-(CH_2)_3O-$ or the trans form of $-CH=CH(CH_2)_2-$ or $-CH=CHCH_2O-$;
n signifies 0 or 1;
m signifies 0 or 1, with the proviso that n+m is <1; and
X signifies cyano, $-CF_3$, $-OCF_3$, $-OCHF_2$, $-CH=CF_2$, $-CH=CHCl$, alkyl, alkenyl, alkoxy, alkenyloxy or alkoxyalkyl with 1 or, respectively, 2 to 6 carbon atoms or on trans-1,4-cyclohexylene also $-CH=CHF$ or $-CH=CHCl$ or on 1,4-phenylene also fluorine or chlorine.

29 Claims, No Drawings

FLUORO-SUBSTITUTED PHENYL-CYCLOHEXYLACETYLENES

This is a continuation of application Ser. No. 08/131,268, filed Oct. 1, 1993, now abandoned.

BACKGROUND OF THE INVENTION

1. Field

The present invention is concerned with novel fluoro-substituted phenyl-cyclohexylacetylenes, their preparation, liquid crystalline mixtures containing such compounds and the use of these compounds and mixtures for electro-optical purposes.

2. Description

Liquid crystals are used primarily as dielectrics in indicating devices, since the optical properties of such substances can be influenced by an applied voltage. Electro-optical devices employing liquid crystals are well-known and can be based on various effects. Such devices include, for example, dynamic scattering cells, DAP cells ("deformation of aligned phases"), guest-/host cells, TN cells ("twisted nematic structure"), STN cells ("super twisted nematic"), SBE cells ("super birefringence effect") and OMI cells ("optical mode interference"). For displays having a high density of information, actively controlled cells, such as TFT ("thin film transistor") cells have recently become an important addition to passively controlled multiplexed cells. However, most common indicator devices are based on the Schadt-Helfrich effect and have a twisted nematic structure.

Liquid crystal materials should have good chemical, photochemical and thermal stability, in addition to good stability towards electric fields. Further, these materials should have a suitable mesophase over a range which is as broad as possible (for example, a nematic or a cholesteric phase for the aforementioned cells) as well as sufficiently high viscosity. When used in cells, liquid crystal materials should permit short response times, low threshold potentials and high contrast. Further properties such as the electrical conductivity, dielectric anisotropy and optical anisotropy should fulfill requirements depending on the field of application and type of cell. For example, materials for cells having a twisted nematic structure should have maximal dielectric anisotropy and minimal conductivity, the latter property being particular important for TFT cells. Components having high dielectric anisotropy and low conductivity are in demand.

Such compounds are provided by the present invention.

SUMMARY OF THE INVENTION

Compounds of the subject invention have the formula:

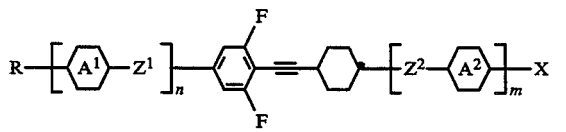

wherein

R is an unsubstituted alkyl, alkoxy, alkenyl or alkenyloxy of 12 or less carbon atoms, or an unsubstituted alkyl, alkoxy, alkenyl or alkenyloxy of 12 or less carbon atoms in which one $CH_2$ group is replaced with oxygen, provided that no two oxygen atoms are directly adjacent, or a fluorine substituted alkyl, alkoxy, alkenyl or alkenyloxy of 12 or less carbon atoms, or a fluorine substituted alkyl, alkoxy, alkenyl or alkenyloxy of 12 or less carbon atoms in which one $CH_2$ group is replaced with oxygen, provided that no two oxygen atoms are directly adjacent;

$A^1$ is 1,4-phenylene, or pyridine-2,5-diyl, or pyrimidine-2,5-diyl, or trans-1,4-cyclohexylene, or trans-1,3-dioxane-2,5-diyl;

$A^2$ is trans-1,4-cyclohexylene, or unsubstituted 1,4-phenylene, or fluorine substituted 1,4-phenylene;

$Z^1$ is a single covalent bond, $-CH_2CH_2-$, $-OCH_2-$, $-CH_2O-$, $-(CH_2)_4-$, $-O(CH_2)_3-$, $-(CH_2)_3O-$ or, when ring $A^1$ is a saturated ring, the trans form of $-CH=CH(CH_2)_2-$ or $-CH=CHCH_2O-$;

$Z^2$ is a single covalent bond, $-CH_2-CH_2-$, $-OCH_2-$, $-CH_2O-$, $-(CH_2)_4-$, $-O(CH_2)_3-$, $-(CH_2)_3O-$, or the trans form of $-CH=CH(CH_2)_2-$ or $-CH=CHCH_2O-$;

n is 0 or 1;

m is 0 or 1, provided that n+m is $\leq 1$; and

X is cyano, $-CF_3$, $-OCF_3$, $-OCHF_2$, $-CH=CF_2$, $-CH=CHCl$, or an unsubstituted alkyl, alkenyl, alkoxy, alkenyloxy or alkoxyalkyl of 6 or less carbon atoms, additionally when $A^2$ is trans-1,4-cyclohexylene, X can also be $-CH=CHF$ or $-CH=CHCl$, and when $A^2$ is 1,4-phenylene, X can also be fluorine or chlorine.

Also provided for are mixtures comprising the above compound, a method of achieving an electro-optical effect by providing the above compound and electronically stimulating the compound to achieve the desired electro-optical effect, and an electro-optical cell having two plate means, liquid crystal means disposed between the plate means and including the above compounds, and means for applying electric potential to the plate means.

DETAILED DESCRIPTION OF THE INVENTION

The invention will now be described in terms of its preferred embodiments. These embodiments are set forth and aid in the understanding of the invention, but are not to be construed as limiting.

The invention is concerned with compounds of formula:

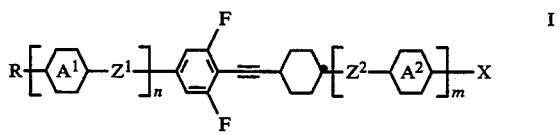

wherein

R signifies alkyl, alkoxy, alkenyl or alkenyloxy with 1 or, respectively, 2 to 12 carbon atoms in which one $CH_2$ group can be replaced by oxygen and/or one or more hydrogen atoms can be replaced by fluorine atoms, with the proviso that two oxygen atoms are not directly adjacent;

$A^1$ represents 1,4-phenylene, pyridine-2,5-diyl, pyrimidine-2,5-diyl, trans-1,4-cyclohexylene or trans-1,3-dioxane-2,5-diyl;

$A^2$ signifies trans-1,4-cyclohexylene, or 1,4-phenylene which is optionally substituted with fluorine;

$Z^1$ signifies a single covalent bond, —CH₂CH₂—, —OCH₂—, —CH₂O—, —(CH₂)₄—, —O(CH₂)₃—, —(CH₂)₃O— or, when ring $A^1$ represents a saturated ring, also the trans form of —CH=CH(CH₂)₂— or —CH=CHCH₂O—;

$Z^2$ signifies a single covalent bond, —CH₂—CH₂—, —OCH₂—, —CH₂O—, —(CH₂)₄—, —O(CH₂)₃—, —(CH₂)₃O— or the trans form of —CH=CH(CH₂)₂— or —CH=CHCH₂O—;

n signifies 0 or 1;

m signifies 0 or 1, with the proviso that n+m is ≦1; and

X signifies cyano, —CF₃, —OCF₃, —OCHF₂, —CH=CF₂, —CH=CHCl, alkyl, alkenyl, alkoxy, alkenyloxy or alkoxyalkyl with 1 or, respectively, 2 to 6 carbon atoms or on trans-1,4-cyclohexylene also —CH=CHF or —CH=CHCl or on 1,4-phenylene also fluorine or chlorine.

The compounds in accordance with the invention are liquid crystals having a pronounced nematic phase, a comparatively high dielectric anisotropy and a relatively low rotation viscosity and lead to comparatively low threshold potentials and short response times. Moreover, in spite of double lateral substitution the clearing point is surprisingly high with a comparatively low melting point and small melting enthalpy. The optical anisotropy can be lowered or increased as desired by suitable choice of a saturated or aromatic ring for $A^1$ or $A^2$. Moreover, the dielectric anisotropy can be influenced by suitable choice of the substituent X.

The compounds in accordance with the invention have a very good solubility in mixtures having wide concentration ranges. They are especially suitable for use in mixtures which should have, in the case of a low threshold potential, a low conductivity and simultaneously a suitable (according to requirements) high or low optical anisotropy, for example for TN, STN or TFT cells.

The term "saturated ring" embraces in the scope of the present invention trans-1,4-cyclohexylene or trans-1,3-dioxane-2,5-diyl.

In the compounds of formula 1 in which $A^1$ signifies a heterocyclic ring such as pyridine-2.5-diyl, pyrimidine-2,5-diyl or trans-1,3-dioxane-2,5-diyl, the hetero atoms in the ring are arranged exclusively such that they occupy a position adjacent to the linkage position with $Z^1$.

The term "1,4-phenylene which is optionally substituted with fluorine" embraces in connection with ring $A^2$ unsubstituted, mono- or difluorinated 1,4-phenylene rings.

The bridging member $Z^1$ preferably signifies a single covalent bond, —CH₂CH₂—, —OCH₂— or —CH₂O—, but especially a single covalent bond or —CH₂CH₂—.

The bridging member $Z^2$ preferably signifies a single covalent bond or —CH₂—CH₂—.

In the compounds of formula 1 in which X signifies alkyl, alkoxy or alkoxyalkyl there are preferred straight-chain residues with 1 or, respectively, 2 to 6 carbon atoms, with residues having 1 or, respectively, 2 to 3 carbon atoms such as, for example methyl, ethyl, propyl, methoxy, ethoxy, propyloxy, methoxymethyl, ethoxymethyl, methoxyethyl and the like being especially preferred.

In the compounds of formula 1 in which X signifies alkenyl or alkenyloxy, straight-chain residues with 2 to 6 carbon atoms are preferred. Preferred alkenyl residues are those in which the double bond is terminal or has the E-configuration and is situated at C(3), or on a trans-1,4-cyclohexylene ring also at C(1 ). Preferred alkenyloxy residues are those having a double bond at C(2) with the E-configuration or those having a terminal double bond. Examples of such residues are vinyl, 1E-propenyl, 1E-butenyl, 1E-pentenyl, 1E-hexenyl, 3-butenyl, 3E-pentenyl, 3E-hexenyl, 4-pentenyl, 5-hexenyl, allyloxy, 2E-butenyloxy and the like.

The term "alkyl, alkoxy, alkenyl or alkenyloxy with 1 or, respectively, 2 to 12 carbon atoms in which one CH₂ group can be replaced by oxygen and/or one or more hydrogen atoms can be replaced by fluorine atoms, with the proviso that two oxygen atoms are not directly adjacent" embraces in the scope of the present invention straight-chain or branched, optionally chiral, alkyl, alkoxy, alkenyl, alkenyloxy, alkoxyalkyl, alkenyloxy, alkenyloxyalkyl and alkyloxyalkenyl residues with 1 or, respectively, 2 to 12 carbon atoms which can be mono- or poly-substituted with fluorine. Unsubstituted, straight-chain residues with 1 or, respectively, 2 to 6 carbon atoms are preferred residues. Preferred alkenyl residues are those in which the double bond has the E-configuration and is situated at C(3) or, when ring $A^1$ represents a saturated ring, also at C(1 ) or is terminal. Preferred alkenyloxy residues are those having a double bond at C(2) with the E-configuration or those having a terminal double bond. Examples of such residues are methyl, ethyl, propyl, butyl, pentyl, hexyl, methoxy, ethoxy, propyloxy, butyloxy, pentyloxy, hexenyloxy, vinyl, 1E-propenyl, 1E-butenyl, 1E-pentenyl, 1E-hexenyl, 3-butenyl, 3E-pentenyl, 3E-hexenyl, 4-pentenyl, 5-hexenyl, allyloxy, 2E-butenyloxy, 3-butenyloxy, methoxymethyl, ethoxymethyl, propyloxymethyl, allyloxymethyl, methoxyethyl, ethoxyethyl, propyloxyethyl, methoxypropyl, ethoxypropyl, methoxy-1E-propenyl, ethoxy-1E-propenyl and the like.

Compounds of the following formulae are especially preferred sub-groups of compounds of formula 1:

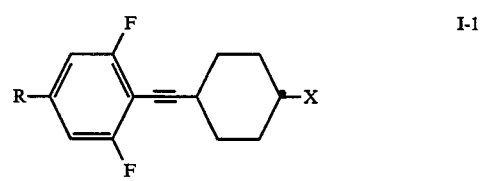

I-1

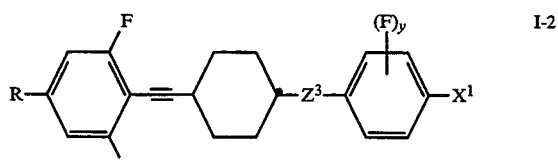

I-2

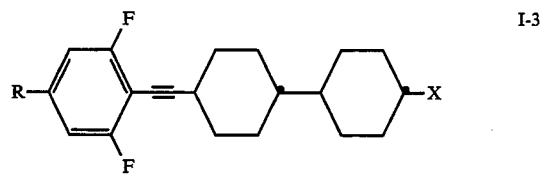

I-3

I-4 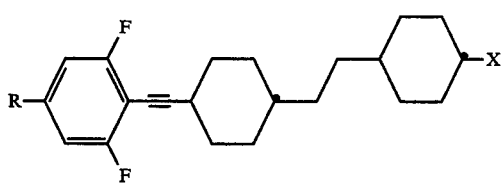

I-5 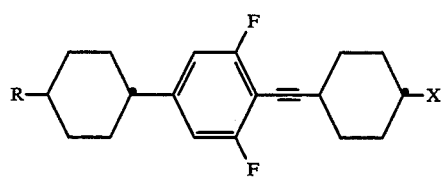

I-6 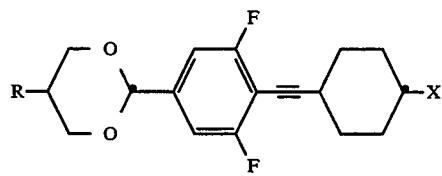

I-7 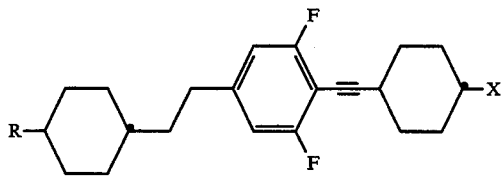

I-8 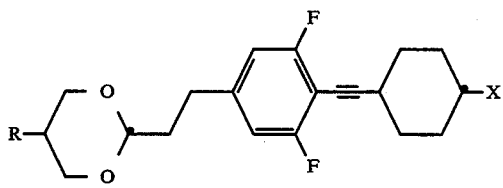

I-9 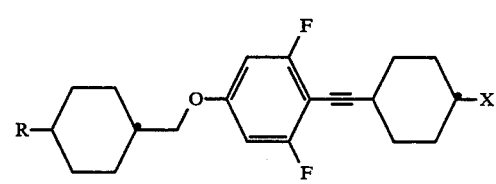

I-10 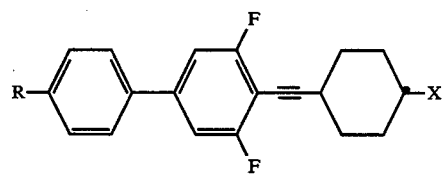

I-11 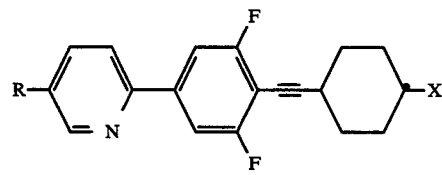

I-12 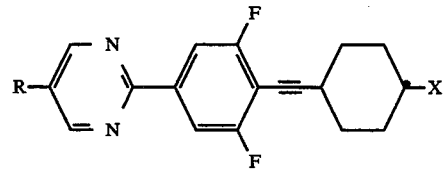

wherein

R signifies alkyl, alkoxy, alkenyl or alkenyloxy with 1 or, respectively, 2 to 6 carbon atoms in which one $CH_2$ group can be replaced by oxygen, with the proviso that two oxygen atoms are not directly adjacent;

X signifies $-OCF_3$, $-OCHF_2$, $-CH=CF_2$, $-CH=CHF$, $-CH=CHCl$ or alkyl, alkenyl, alkoxy or alkenyloxy with 1 or, respectively, 2 to 3 carbon atoms;

$X^1$ signifies fluorine, chlorine, cyano, $-OCHF_2$ or $-CH=CF_2$;

$Z^3$ signifies a single covalent bond or $-CH_2CH_2-$;

Y signifies 0, 1 or 2; and the phenyl ring

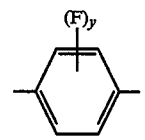

is unsubstituted or substituted as follows

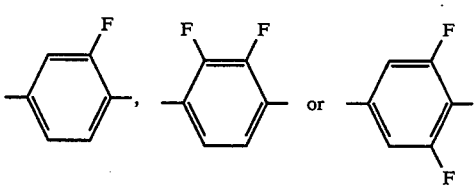

Particularly preferred compounds of formula 1-2 are those in which $X^1$ signifies fluorine, chlorine or cyano.

Further particularly preferred compounds of formula 1 are compound of formulae 1-3 to 1-10, especially compound of formula 1-3 to 1-8, in which X signifies alkyl or alkenyl with 1 or, respectively, 2 to 3 carbon atoms, such as, for example, methyl, ethyl, propyl, vinyl or 1E-propenyl, as well as $-CH=CF_2$, $-CH=CHF$ or $-CH=CHCl$.

The preparation of the compounds of formula 1 may be effected in a known manner. It is set forth in the following Scheme in which the substituents given in formulae I–VI have the aforementioned significance. The halogenation of a compound of formula II with bromine or iodine to give compounds of formula III is preferably carried out in an inert solvent (e.g. tetrahydrofuran, ether, dimethoxyethane etc.) at a low temperature (e.g. in a range of −70° to −40°).

Metal-catalyzed couplings of phenyl compounds with acetylenes, as in the last step for the preparation of I from III, are well-known from the literature, e.g. C. Pogh and V. Percey, *Mol. Cryst. Liq. Cryst.* (1990) 178: 193, the contents, of which are herein incorporated by reference. They can be carried out, as mentioned earlier, with bromides and iodides, but in certain cases also with trifluorosulphonates and chlorides. The cyclohexylacetylenes of formula VI are known compounds or analogs of known compounds; such compounds are described, for example in U.S. Pat. Nos. 4,565,425, 4,676,604 and 5,01 3,478, the contents of which are herein incorporated by reference. Preparation is readily determinable by a person skilled in the art and may be effected according to usual methods, for example according to the route set forth in the Scheme. Thus, a trans-cyclohexylcarboxaldehyde of formula IV can subjected to a Wittig reaction with tetrabromomethane and triphenylphosphine and the resulting 2,2-dibromovinylcyclohexane V can be converted with butyllithium into the acetylene VI. Aldehydes of formula IV or analogous aldehydes will be known to a person skilled in the art and can be prepared according to known methods. Many of them have been described as intermediates for the preparation of liquid crystals, for example in M. Petrzilka and A. Germann, *Mol. Cryst. Liq. Cryst.* (1985) 131: 327, the contents of which are herein incorporated by reference.

are therefore those which additionally contain one or more compounds having positive dielectric anisotropy.

Having regard to the good solubility of the compounds of formula 1 in other liquid crystal materials and having regard to their good miscibility with one another, the content of compounds of formula 1 in the mixtures in accordance with the invention can be relatively high and can be, for example, about 1–70 wt. %. In general, a content of about 3–40 wt. %, especially 5–30 wt. %, of compounds of formula 1 is preferred.

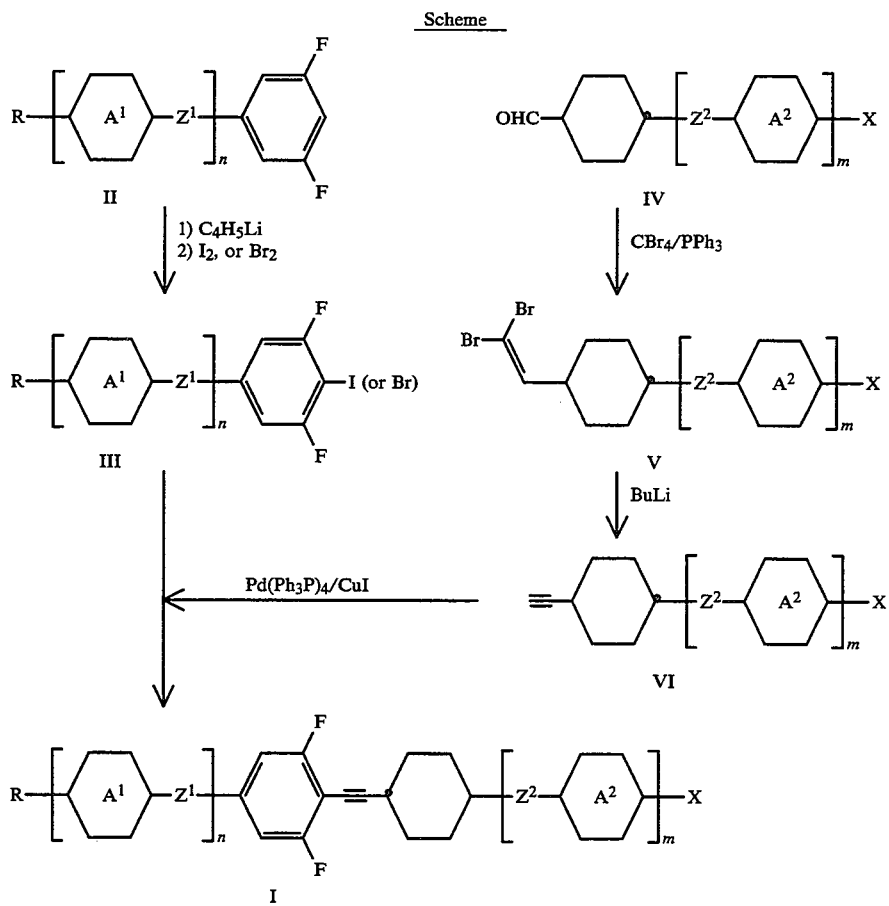

The synthesis of those compounds of formula II in which n=1 is effected in complete analogy to the isomeric 3,4-difluorophenyl compounds which will be familiar as liquid crystals to a person skilled in the art. The compounds of formula II in which n=0 can be prepared readily according to known methods, e.g. by a Wittig reaction and subsequent catalytic hydrogenation or by etherification from commercially available 3,5-difluorobenzaldehyde or 3,5-difluorophenol.

The liquid crystalline mixtures in accordance with the invention may contain at least two components, with at least one component being a compound of formula 1. A second component and optionally additional components can be further compounds of formula 1 and/or other suitable liquid crystal components.

The compounds of formula 1 are especially suitable for nematic mixtures or, insofar as at least one component of the mixture is optically active, also for cholesteric mixtures. A preferred application comprises their use as dielectrics in liquid crystal indicator devices having a twisted nematic liquid crystal structure such as TN cells, STN cells and TFT cells. Preferred mixtures The mixtures in accordance with the invention preferably contain, in addition to one or more compounds of formula 1, one or more compounds of formulae:

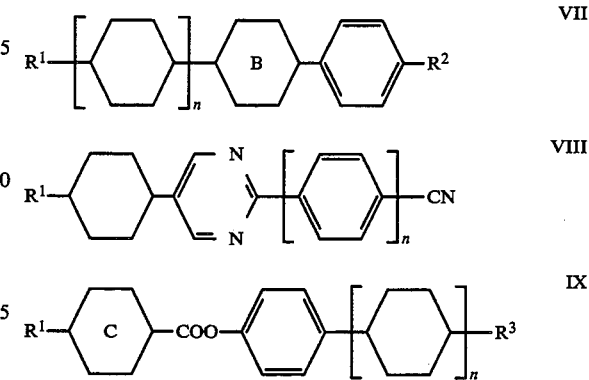

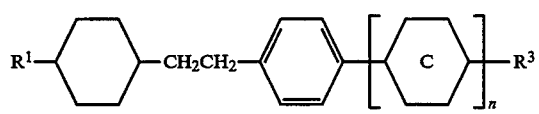
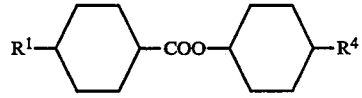
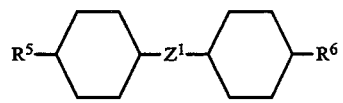
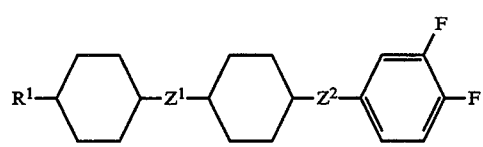
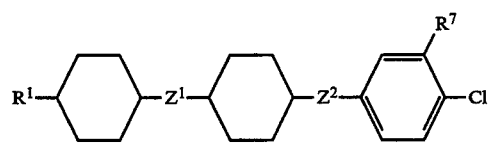
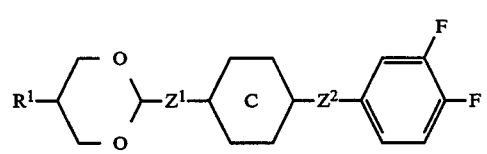
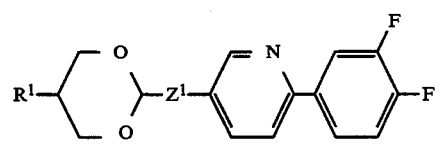
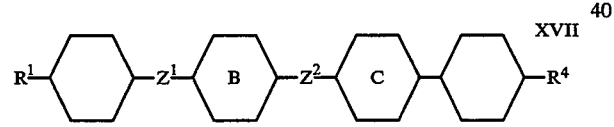
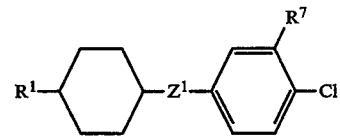
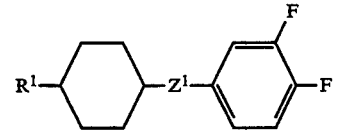
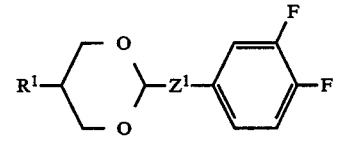
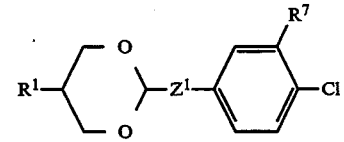
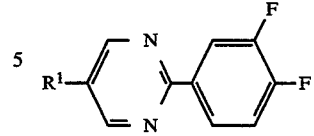
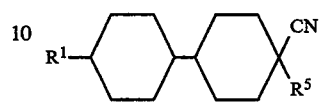
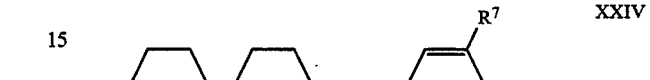

wherein $R^1$, $R^4$ signify alkyl, alkoxyalkyl, 3E-alkenyl, 4-alkenyl or on saturated rings also 1E-alkenyl;

n signifies 0 or 1;

ring B denotes 1,4-phenylene, pyridine-2,5-diyl, pyrimidine-2,5-diyl, trans-1,4-cyclohexylene or trans-1,3-dioxane-2,5-diyl;

$R^2$ represents cyano, isothiocyanato, fluorine, alkyl, 3E-alkenyl, 4-alkenyl, alkoxy, 2E-alkenyloxy, 3-alkenyloxy or 1-akynyl;

ring C signifies 1,4-phenylene or trans-1,4-cyclohexylene;

$R^3$ denotes alkyl, 3E-alkenyl, 4-alkenyl or on trans-1,4-cyclohexylene also 1E-alkenyl or on 1,4-phenylene also cyano, isothiocyanato, alkoxy, 2E-alkenyloxy or 3-alkenyloxy;

$R^5$ signifies alkyl, 1E-alkenyl, 3E-alkenyl or 4-alkenyl;

$R^6$ represents cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl;

$Z^1$, $Z^2$ each independently denote a single covalent bond or —$CH_2CH_2$—, with two aromatic rings always being linked by a single covalent bond;

$R^7$ signifies hydrogen, fluorine or chlorine;

$R^8$ represents cyano, fluorine or chlorine;

$R^9$ denotes hydrogen of fluorine; and $R^{10}$ represents fluorine or chlorine.

The above term "saturated ring" embraces trans-1,4-cyclohexylene and trans-1,3-dioxane-2,5-diyl. The residues $R^1$ to $R^6$ each preferably have 1 or, respectively, 2 to 12 carbon atoms, especially 1 or, respectively, 2 to 7 carbon atoms. Straight-chain residues are generally preferred.

The term "alkyl" preferably signifies in this connection straight-chain residues with 1 to 12 carbon atoms, preferably with 1 to 7 carbon atoms, such as, for example, methyl, ethyl, propyl, butyl, pentyl, hexyl, heptyl and the like.

The term "alkyloxyalkyl" preferably signifies in this connection straight-chain residues with 1 to 12 carbon atoms, especially with 1 to 7 carbon atoms, such as, for example, methoxymethyl, ethoxymethyl, propyloxymethyl, butyloxymethyl, methoxypropyl and the like.

The term "alkoxy" preferably signifies in this connection straight-chain residues with 1 to 12 carbon atoms, especially with 1 to 7 carbon atoms, such as, for example, methoxy, ethoxy, propyloxy, butyloxy, pentyloxy, hexyloxy, heptyloxy and the like.

The term "1E-alkenyl" preferably signifies in this connection straight-chain alkenyl residues with 2 to 12, especially with 2 to 7, carbon atoms in which the double bond is situated in the 1-position, such as, for example, vinyl, 1E-propenyl, 1E-butenyl, 1E-pentenyl, 1E-hexenyl, 1E-heptenyl and the like.

The term "3E-alkenyl" preferably signifies in this connection straight-chain alkenyl residues with 4 to 12, especially with 4 to 7, carbon atoms in which the double bond is situated in the 3-position, such as, for example, 3-butenyl, 3E-pentenyl, 3E-hexenyl, 3E-heptenyl and the like.

The term "4-alkenyl" preferably signifies in this connection straight-chain alkenyl residues with 5 to 12 carbon atoms in which the double bond is situated in the 4-position, such as, for example, 4-pentenyl, 4-hexenyl, 4-heptenyl and the like.

The term "2E- or 3-alkenyloxy" preferably signifies in this connection straight-chain alkenyloxy residues with 3 or 4 to 12 carbon atoms, especially with 3 or 4 to 7 carbon atoms, in which the double bond is situated in the 2- or 3-position and E indicates the preferred configuration, such as, for example, allyloxy, 2E-butenyloxy, 2E-pentenyloxy, 2E-hexenyloxy, 2E-heptenyloxy, 3-butenyloxy, 3-pentenyloxy, 3-hexenyloxy, 3-heptenyloxy, 4-pentenyloxy, 5-hexenyloxy, 6-heptenyloxy and the like.

The term "1-alkynyl" preferably signifies in this connection straight-chain alkynyl residues with 2 to 12, especially with 2 to 7, carbon atoms in which the triple bond is situated in the 1-position, such as, for example, ethynyl, 1-propynyl, 1-butynyl, 1-pentynyl and the like.

The manufacture of the liquid crystalline mixtures and of the electro-optical devices can be effected using techniques readily determinable by one skilled in the art.

The invention is illustrated in more detail by the following Examples. In the Examples, C signifies a crystalline phase, N signifies a nematic phase, S signifies a smectic phase and I signifies the isotropic phase. $V_{10}$ denotes the voltage for 10% transmission; $t_{on}$ and $t_{off}$ denote, respectively, the switching-on time and the switching-off time and $\Delta n$ denotes the optical anisotropy.

Unless indicated otherwise, all Examples were carried out as written. All compounds expressing melting point, or other data, whenever noted in the specification have actually been synthesized.

Example 1 a) 5.9 ml of a 1.6N butyllithium solution in hexane are added dropwise during 20 min. to a solution of 2.14 g of 1-(trans-4-propylcyclohexyl)-3,5-difluorobenzene in 20 ml of dry tetrahydrofuran at −70° C. and the mixture is left to react at −70° C. for 1 hr. Then, a solution of 2.4 g of iodine in 10 ml of dry tetrahydrofuran is added dropwise within 10 min. at −60° and the mixture is gradually warmed to room temperature over a period of a further 30 min. The resulting yellow solution is thereafter treated with 10 ml of water and then with 10 ml of a 10 percent aqueous sodium bicarbonate solution and extracted with ether. The ether solution is washed with saturated sodium chloride solution and several times with water, dried over magnesium sulphate, filtered and concentrated. Chromatography of the residue over 150 g of silica gel with hexane gives 3.27 g of 1-(trans-4-propylcyclohexyl)-3,5-difluoro-4-iodobenzene as a colorless liquid.

b) A mixture of 0.8 g of 1-(trans-4-propylcyclohexyl)-3,5-difluoro-4-iodobenzene, 0.379 g of trans-1-ethynyl-4-propylcyclohexane, 0.023 g of tetrakis(triphenylphosphine)palladium(0) and 0.009 g of copper(I) iodide in 20 ml of triethylamine is stirred at 105° C. for 17 hrs. Thereafter, the mixture is cooled, partitioned between ether and water, the combined organic phases are dried over magnesium sulphate, filtered and the filtrate is evaporated on a rotary evaporator. Chromatography on 140 g of silica gel with hexane and three-fold crystallization from methanol, hexane and again methanol gives 0.376 g of 1-(trans-4-propylcyclohexylethynyl)-2,6-difluoro-4-(trans-4-propylcyclohexyl)-benzene, m.p. (C/N) 120.2° C., cl.p. (N/I) 171.4° C.

The following compounds can be prepared in an analogous manner:

1-(trans-4-Ethylcyclohexylethynyl)-2,6-difluoro-4-propylbenzene, m.p. (C/I) 1.2° C., cl.p. (N/I) −43° C. (virt.);

1-(trans-4-ethylcyclohexylethynyl)-2,6-difluoro-4-butylbenzene;

1-(trans-4-ethylcyclohexylethynyl)-2,6-difluoro-4-pentylbenzene;

1-(trans-4-vinylcyclohexylethynyl)-2,6-difluoro-4-propylbenzene;

1-(trans-4-propylcyclohexylethynyl)-2,6-difluoro-4-propylbenzene;

1-(trans-4-propylcyclohexylethynyl)-2,6-difluoro-4-butylbenzene;

1-(trans-4-propylcyclohexylethynyl)-2,6-difluoro-4-pentylbenzene;

1-(trans-4-butylcyclohexylethynyl)-2,6-difluoro-4-propylbenzene;

1-(trans-4-methoxycyclohexylethynyl)-2,6-difluoro-4-propylbenzene;

1-(trans-4-ethoxycyclohexylethynyl)-2,6-difluoro-4-propylbenzene, m.p. (C/N) 41.8° C., cl.p. (N/I) −80° C. (virt.);

1-(trans-4-difluoromethoxycyclohexylethynyl)-2,6-difluoro-4-propylbenzene;

1-(trans-4-trifluoromethoxycyclohexylethynyl)-2,6-difluoro-4-propylbenzene;

1-[trans-4-(2-fluorovinyl)cyclohexylethynyl]-2,6-difluoro-4-propylbenzene;

1-[trans-4-(2,2-difluorovinyl)cyclohexylethynyl]-2,6-difluoro-4-propylbenzene, cl.p. (N/I) −35° C. (virt.);

1-[trans-4-(2-fluorovinyl)cyclohexylethynyl]-2,6-difluoro-4-butylbenzene;

1-[trans-4-(2,2-difluorovinyl)cyclohexylethynyl]-2,6-difluoro-4-butylbenzene;

1-[trans-4-(2-fluorovinyl)cyclohexylethynyl]-2,6-difluoro-4-(3-butenyl)benzene;

1-[trans-4-(2,2-difluorovinyl)cyclohexylethynyl]-2,6-difluoro-4-(3-butenyl)benzene;

1-[trans-4-(2,2-difluorovinyl)cyclohexylethynyl]-2,6-difluoro-4-pentylbenzene;

1-[trans-4-(2-fluorovinyl)cyclohexylethynyl]-2,6-difluoro-4-pentylbenzene;

1-[trans-4-(2,2-difluorovinyl)cyclohexylethynyl]-2,6-difluoro-4-(4-pentenyl)benzene;
1-[trans-4-(2-fluorovinyl)cyclohexylethynyl]-2,6-difluoro-4-(4-pentenyl)benzene;
1-[trans-4-(2-E-chlorovinyl)cyclohexylethynyl]-2,6-difluoro-4-propylbenzene;
1-[trans-4-(2-E-chlorovinyl)cyclohexylethynyl]-2,6-difluoro-4-butylbenzene;
1-[trans-4-(2-E-chlorovinyl)cyclohexylethynyl]-2,6-difluoro-4-(3-butenyl)benzene;
1-[trans-4-(2-E-chlorovinyl)cyclohexylethynyl]-2,6-difluoro-4-pentylbenzene;
1-[trans-4-(2-E-chlorovinyl)cyclohexylethynyl]-2,6-difluoro-4-(4-pentenyl)benzene;
1-(trans-4-ethylcyclohexylethynyl)-2,6-difluoro-4-(trans-4-propylcyclohexyl)benzene, m.p. (C/N) 86.3° C., cl.p. (N/I) 152.2° C.;
1-(trans-4-ethylcyclohexylethynyl)-2,6-difluoro-4-(trans-4-butylcyclohexyl)benzene;
1-(trans-4-ethylcyclohexylethynyl)-2,6-difluoro-4-(trans-4-pentylcyclohexyl)benzene;
1-(trans-4-propylcyclohexylethynyl)-2,6-difluoro-4-(trans-4-butylcyclohexyl)benzene;
1-(trans-4-propylcyclohexylethynyl)-2,6-difluoro-4-(trans-4-pentylcyclohexyl)benzene;
1-(trans-4-butylcyclohexylethynyl)-2,6-difluoro-4-(trans-4-propylcyclohexyl)benzene, m.p. (C/N) 93.6° C., cl.p. (N/I) 167° C.;
1-(trans-4-butylcyclohexylethynyl)-2,6-difluoro-4-(trans-4-butylcyclohexyl)benzene;
1-(trans-4-butylcyclohexylethynyl)-2,6-difluoro-4-(trans-4-pentylcyclohexyl)benzene;
1-(trans-4-vinylcyclohexylethynyl)-2,6-difluoro-4-(trans-4-propylcyclohexyl)benzene;
1-(trans-4-difluoromethoxycyclohexylethynyl)-2,6-difluoro-4-(trans-4-propylcyclohexyl)benzene;
1-(trans-4-ethylcyclohexylethynyl)-2,6-difluoro-4-(trans-4-vinylcyclohexyl)benzene;
1-(trans-4-ethylcyclohexylethynyl)-2,6-difluoro-4-[trans-4-(1-E-propenyl)cyclohexyl]benzene;
1-(trans-4-ethylcyclohexylethynyl)-2,6-difluoro-4-[trans-4-(3-butenyl)cyclohexyl]benzene;
1-(trans-4-ethylcyclohexylethynyl)-2,6-difluoro-4-[trans-4-(4-pentenyl)cyclohexyl]benzene;
1-[trans-4-(2-fluorovinyl)cyclohexylethynyl]-2,6-difluoro-4-(trans-4-ethylcyclohexyl)benzene;
1-[trans-4-(2,2-difluorovinyl)cyclohexylethynyl]-2,6-difluoro-4-(trans-4-ethylcyclohexyl)benzene;
1-[trans-4-(2-fluorovinyl)cyclohexylethynyl]-2,6-difluoro-4-(trans-4-propylcyclohexyl)benzene;
1-[trans-4-(2,2-difluorovinyl)cyclohexylethynyl]-2,6-difluoro-4-(trans-4-propylcyclohexyl)benzene, m.p. (C/N) 53.1° C., (N/C<35° C.), cl.p. (N/I) 169.9° C.;
1-[trans-4-(2-fluorovinyl)cyclohexylethynyl]-2,6-difluoro-4-(trans-4-pentylcyclohexyl)benzene;
1-[trans-4-(2,2-difluorovinyl)cyclohexylethynyl]-2,6-difluoro-4-(trans-4-pentylcyclohexyl)benzene;
1-[trans-4-(2-E-chlorovinyl)cyclohexylethynyl]-2,6-difluoro-4-(trans-4-propylcyclohexyl)benzene;
1-[trans-4-(2-E-chlorovinyl)cyclohexylethynyl]-2,6-difluoro-4-(trans-4-pentylcyclohexyl)benzene;
1-(trans-4-methoxycyclohexylethynyl])-2,6-difluoro-4-(trans-4-propylcyclohexyl)benzene;
1-(trans-4-ethoxycyclohexylethynyl])-2,6-difluoro-4-(trans-4-propylcyclohexyl)benzene, m.p. (C/N) 93.3° C., cl.p. (N/I) 112.1° C.;
1-(trans-4-difluoromethoxycyclohexylethynyl)-2,6-difluoro-4-(trans-4-propylcyclohexyl)benzene;
1-(trans-4-trifluoromethoxycyclohexylethynyl])-2,6-difluoro-4-(trans-4-propylcyclohexyl)benzene;
1-(trans-4-cyanocyclohexylethynyl)-2,6-difluoro-4-(trans-4-propylcyclohexyl)benzene;
1-(trans-4-ethylcyclohexylethynyl)-2,6-difluoro-4-(trans-5-propyl-1,3-dioxan-2-yl)benzene;
1-(trans-4-ethylcyclohexylethynyl)-2,6-difluoro-4-(trans-5-pentyl-1,3-dioxan-2-yl)benzene;
1-(trans-4-ethylcyclohexylethynyl)-2,6-difluoro-4-[trans-5-(1-E-propenyl)-1,3-dioxan-2-yl]benzene;
1-(trans-4-propylcyclohexylethynyl)-2,6-difluoro-4-[trans-5-(4-pentenyl)-1,3-dioxan-2-yl]benzene;
1-[trans-4-(2-fluorovinyl)cyclohexylethynyl]-2,6-difluoro-4-(trans-5-propyl-1,3-dioxan-2-yl)benzene;
1-[trans-4-(2,2-difluorovinyl)cyclohexylethynyl]-2,6-difluoro-4-(trans-5-propyl-1,3-dioxan-2-yl)benzene;
1-[trans-4-1-E-chlorovinyl)cyclohexylethynyl]-2,6-difluoro-4-(trans-5-propyl-1,3-dioxan-2-yl)benzene;
1-(trans-4-ethylcyclohexylethynyl)-2,6-difluoro-4-(4-propylphenyl)benzene;
1-(trans-4-ethylcyclohexylethynyl)-2,6-difluoro-4-(4-butylphenyl)benzene;
1-(trans-4-propylcyclohexylethynyl)-2,6-difluoro-4-(4-butylphenyl)benzene;
1-(trans-4-propylcyclohexylethynyl)-2,6-difluoro-4-(4-pentylphenyl)benzene;
1-(trans-4-propylcyclohexylethynyl)-2,6-difluoro-4-[4-(4-pentenyl)phenyl]benzene;
1-(trans-4-propylcyclohexylethynyl)-2,6-difluoro-4-(4-propyloxyphenyl)benzene;
1-[trans-4-(2-fluorovinyl)cyclohexylethynyl]-2,6-difluoro-4-(4-propylphenyl)benzene;
1-[trans-4-(2,2-difluorovinyl)cyclohexylethynyl]-2,6-difluoro-4-(4-propylphenyl)benzene;
1-[trans-4-(2-E-chlorovinyl)cyclohexylethynyl]-2,6-difluoro-4-(4-propylphenyl)benzene;
1-[trans-4-ethylcyclohexylethynyl]-2,6-difluoro-4-(5-propylpyrimidin-2-yl)benzene;
1-[trans-4-propylcyclohexylethynyl]-2,6-difluoro-4-(5-butylpyrimidin-2-yl)benzene;
1-[trans-4-propylcyclohexylethynyl]-2,6-difluoro-4-(5-pentylpyrimidin-2-yl)benzene;
1-[trans-4-butylcyclohexylethynyl]-2,6-difluoro-4-(5-propylpyrimidin-2-yl)benzene;
1-[trans-4-(2-fluorovinyl)cyclohexylethynyl]-2,6-difluoro-4-(5-pentylpyrimidin-2-yl)benzene;
1-[trans-4-(2,2-difluorovinyl)cyclohexylethynyl]-2,6-difluoro-4-(5-pentylpyrimidin-2-yl)benzene;
1-[trans-4-(2-E-chlorovinyl)cyclohexylethynyl]-2,6-difluoro-4-(5-pentylpyrimidin-2-yl)benzene;
1-[trans-4-ethylcyclohexylethynyl]-2,6-difluoro-4-(5-propylpyridin-2-yl)benzene;
1-[trans-4-butylcyclohexylethynyl]-2,6-difluoro-4-(5-propylpyridin-2-yl)benzene;
1-[trans-4-(2-fluorovinyl)cyclohexylethynyl]-2,6-difluoro-4-(5-propylpyridin-2-yl)benzene;
1-[trans-4-(2,2-difluorovinyl)cyclohexylethynyl]-2,6-difluoro-4-(5-propylpyridin-2-yl)benzene;
1-[trans-4-(2-E-chlorovinyl)cyclohexylethynyl]-2,6-difluoro-4-(5-pentylpyridin-2-yl)benzene;
1-(trans-4-ethylcyclohexylethynyl)-2,6-difluoro-4-[2-(trans-4-propylcyclohexyl)ethyl]benzene;
1-(trans-4-ethylcyclohexylethynyl)-2,6-difluoro-4-[2-(trans-4-butylcyclohexyl)ethyl]benzene;
1-(trans-4-ethylcyclohexylethynyl)-2,6-difluoro-4-[2-(trans-4-pentylcyclohexyl)ethyl]benzene;
1-(trans-4-ethylcyclohexylethynyl)-2,6-difluoro-4-[2-(trans-4-(3-butenyl)cyclohexyl)ethyl]benzene;

1-(trans-4-vinylcyclohexylethynyl)-2,6-difluoro-4-[2-(trans-4-propylcyclohexyl)ethyl]benzene;
1-(trans-4-propylcyclohexylethynyl)-2,6-difluoro-4-[2-(trans-4-propylcyclohexyl)ethyl]benzene;
1-[trans-4-(2-fluorovinyl)cyclohexylethynyl]-2,6-difluoro-4-[2-(trans-4-propylcyclohexyl)ethyl]benzene;
1-[trans-4-(2,2-difluorovinyl)cyclohexylethynyl]-2,6-difluoro-4-[2-(trans-4-propylcyclohexyl)ethyl]benzene;
1-[trans-4-(2-E-chlorovinyl)cyclohexylethynyl]-2,6-difluoro-4-[2-(trans-4-butylcyclohexyl)ethyl]benzene;
1-(trans-4-ethylcyclohexylethynyl)-2,6-difluoro-4-[2-(trans-5-propyl-1,3-dioxan-2-yl)ethyl]benzene;
1-(trans-4-ethylcyclohexylethynyl)-2,6-difluoro-4-[2-(trans-5-butyl-1,3-dioxan-2-yl)ethyl]benzene;
1-(trans-4-ethylcyclohexylethynyl)-2,6-difluoro-4-[2-(trans-5-(3-butenyl)-1,3-dioxan-2-yl)ethyl]benzene;
1-(trans-4-ethylcyclohexylethynyl)-2,6-difluoro-4-[2-(trans-5-pentyl-1,3-dioxan-2-yl)ethyl]benzene;
1-(trans-4-vinylcyclohexylethynyl)-2,6-difluoro-4-[2-(trans-5-propyl-1,3-dioxan-2-yl)ethyl]benzene;
1-(trans-4-propylcyclohexylethynyl)-2,6-difluoro-4-[2-(trans-5-propyl-1,3-dioxan-2-yl)ethyl]benzene;
1-[trans-4-(2-fluorovinyl)cyclohexylethynyl]-2,6-difluoro-4-[2-trans-5-propyl-1,3-dioxan-2-yl)ethyl]benzene;
1-[trans-4-(2,2-difluorovinyl)cyclohexylethynyl]-2,6-difluoro-4-[2-(trans-5-propyl-1,3-dioxan-2-yl)ethyl]benzene;
1-[trans-4-(2-E-chlorovinyl)cyclohexylethynyl]-2,6-difluoro-4-[2-(trans-5-butyl-1,3-dioxan-2-yl)ethyl]benzene;

Example 2

A mixture of 0.65 g of 1-propyl-3,5-difluoro-4-iodobenzene (prepared according to Example 1a), 0.56 g of trans-4-[trans-4-(3-butenyl)cyclohexyl]cyclohexylacetylene, 0.053 g of tetrakis(triphenylphosphine)palladium (0), 0.009 g of copper(I) iodide and 6 ml of triethylamine was heated to 90° C. for 17 hrs. The reaction mixture was cooled, partioned between water and ether, the organic phase was separated and the aqueous phase was extracted several times with ether. The combined organic phases were dried over magnesium sulphate, filtered and evaporated. chromatography of the residue on silica gel with hexane and two-fold crystallization, firstly from hexane and then from isopropanol, gave 640 mg of 1-{trans-4-[trans-4-(3-butenyl)cyclohexyl]cyclohexylethynyl}-2,6-difluoro-4-propylbenzene, m.p. (C/N) 48.5° C., cl.p. (N/I) 189.8° C.

The following compounds can be prepared in an analogous manner:

1-[trans-4-(trans-4-Ethylcyclohexyl)cyclohexylethynyl]-2,6-difluoro-4-propylbenzene, m.p. (C/N) 41.6° C., (N/C)<35° C.), Klp. (N/I) 163.1 ° C.;
1-[trans-4-(trans-4-ethylcyclohexyl)cyclohexylethynyl]-2,6-difluoro-4-butylbenzene;
1-[trans-4-(trans-4-propylcyclohexyl)cyclohexylethynyl]-2,6-difluoro-4-pentylbenzene;
1-[trans-4-(trans-4-ethylcyclohexyl)cyclohexylethynyl]-2,6-difluoro-4-(4-pentenyl)benzene;
1-[trans-4-(trans-4-vinylcyclohexyl)cyclohexylethynyl]-2,6-difluoro-4-propylbenzene, m.p. (C/N) 48.8° C., cl.p. (N/I) 181.1° C.;
1-{trans-4-[trans-4-(3-butenyl)cyclohexyl]cyclohexylethynyl}-2,6-difluoro-4-propylbenzene, m.p. (C/N) 48° C., cl.p. (N/I) 189.8° C.;
1-{trans-4-[trans-4-(4-pentenyl)cyclohexyl]cyclohexylethynyl}-2,6-difluoro-4-propylbenzene, m.p. (C/N) 31.7° C., cl.p. (N/I) 182° C.;
1-[trans-4-(trans-4-vinylcyclohexyl)cyclohexylethynyl]-2,6-difluoro-4-ethoxybenzene, m.p. (C/N) 99° C., cl.p. (N/I) 219,6° C.;
1-{trans-4-[trans-4-(2-fluorovinyl)cyclohexyl]cyclohexylethynyl}-2,6-difluoro-4-propylbenzene;
1-{trans-4-[trans-4-(2,2-difluorovinyl)cyclohexyl]cyclohexylethynyl}-2,6-difluoro-4-propylbenzene, m.p. (C/N) 51.5° C., cl.p. (N/I) 197.6° C.;
1-{trans-4-[trans-4-(2-E-chlorovinyl)cyclohexyl]cyclohexylethynyl}-2,6-difluoro-4-propylbenzene, m.p. (C/N) 80.2° C., cl.p. (N/I) 245.5° C.;
1-{trans-4-[trans-4-(2-E-chlorovinyl)cyclohexyl]cyclohexylethynyl}-2,6-difluoro-4-ethoxybenzene, m.p. (C/N) 102.1° C., cl.p. (N/I) 287.5° C.;
1-[trans-4-(trans-4-methoxycyclohexyl)cyclohexylethynyl]-2,6-difluoro-4-propylbenzene;
1-[trans-4-(trans-4-methoxymethylcyclohexyl)cyclohexylethynyl]-2,6-difluoro-4-propylbenzene;
1-[trans-4-(trans-4-allyloxycyclohexyl)cyclohexylethynyl]-2,6-difluoro-4-propylbenzene;
1-[trans-4-(trans-4-ethylcyclohexyl)cyclohexylethynyl]-2,6-difluoro-4-butyloxybenzene;
1-{trans-4-[2-(trans-4-propylcyclohexyl)ethyl]cyclohexylethynyl}-2,6-difluoro-4-propylbenzene, m.p. (C/N) 64° C., cl.p. (N/I) 153.8° C.;
1-{trans-4-[2-(trans-4-propylcyclohexyl)ethyl]cyclohexylethynyl}-2,6-difluoro-4-propylbenzene;
1-{trans-4-[2-(trans-4-ethylcyclohexyl)ethyl]cyclohexylethynyl}-2,6-difluoro-4-pentylbenzene;
1-{trans-4-[2-(trans-4-vinylcyclohexyl)ethyl]cyclohexylethynyl}-2,6-difluoro-4-propylbenzene;
1-{trans-4-[2-(trans-4-(2-fluorvinyl)cyclohexyl)ethyl]cyclohexylethynyl}-2,6-difluoro-propylbenzene;
1-{trans-4-[2-(trans-4-(2,2-difluorovinyl)cyclohexyl)ethyl]cyclohexyl-ethynyl}-2,6-difluoro-4-propylbenzene;
1-[trans-4-(4-ethylphenyl)cyclohexylethynyl]-2,6-difluoro-4-propylbenzene;
1-[trans-4-(4-trifluoromethylphenyl)cyclohexylethynyl]-2,6-difluoro-4-propylbenzene;
1-[trans-4-(4-methoxyphenyl)cyclohexylethynyl]-2,6-difluoro-4-propylbenzene;
1-[trans-4-(4-difluoromethoxyphenyl)cyclohexylethynyl]-2,6-difluoro-4-propylbenzene;
1-[trans-4-(4-trifluoromethoxyphenyl)cyclohexylethynyl]-2,6-difluoro-4-propylbenzene;
1-[trans-4-(4-cyanophenyl)cyclohexylethynyl]-2,6-difluoro-4-propylbenzene;
1-[trans-4-(4-fluorophenyl)cyclohexylethynyl]-2,6-difluoro-4-propylbenzene;
1-[trans-4-(4-chlorophenyl)cyclohexylethynyl]-2,6-difluoro-4-propylbenzene;
1-[trans-4-(3,4-difluorophenyl)cyclohexylethynyl]-2,6-difluoro-4-ethylbenzene, m.p. (C/I) 71.7° C., cl.p. (N/I) 61.2° C.;
1-[trans-4-(3,4-difluorophenyl)cyclohexylethynyl]-2,6-difluoro-4-propylbenzene, m.p. (C/N) 54.4° C., cl.p. (N/I) 70.2° C.;
1-[trans-4-(3,4-difluorophenyl)cyclohexylethynyl]-2,6-difluoro-4-butylbenzene, m.p. (C/I) 47.5° C., cl.p. (N/I) 62° C.;

1-[trans-4-(3-fluoro-4-chlorophenyl)cyclohexylethynyl]-2,6-difluoro-4-propylbenzene, m.p. (C/I) 65° C., cl.p. (N/I) 114.3° C.;
1-[trans-4-(3-fluoro-4-cyanophenyl)cyclohexylethynyl]-2,6-difluoro-4-propylbenzene;
1-[trans-4-(3-fluoro-4-difluoromethoxyphenyl)cyclohexylethynyl]-2,6-difluoro-4-propylbenzene;
1-[trans-4-(3,4,5-trifluorophenyl)cyclohexylethynyl]-2,6-difluoro-4-ethylbenzene, m.p. (C/I) 77.1° C., cl.p. (N/I)<45° C.;
1-[trans-4-(3,4,5-trifluorophenyl)cyclohexylethynyl]-2,6-difluoro-4-propylbenzene, m.p. (C/I) 63.7° C., cl.p. (N/I)<20° C.;
1-[trans-4-(3,4,5-trifluorophenyl)cyclohexylethynyl]-2,6-difluoro-4-butylbenzene, m.p. (C/I) 77.1° C., cl.p. (N/I)<25° C.;
1-[trans-4-(3,5-difluoro-4-chlorophenyl)cyclohexylethynyl]-2,6-difluoro-4-propylbenzene, m.p. (C/I) 83.5° C., cl.p. (N/I) 80° C.;
1-[4-trans-4-(3,5-difluoro-4-trifluoromethylphenyl)cyclohexylethynyl]-2,6-difluoro-4-propylbenzene, m.p. (C/I) 123.4° C., cl.p. −15° (virt.);
1-[trans-4-(2,3,4-trifluorophenyl)cyclohexylethynyl]-2,6-difluoro-4-propylbenzene;
1-{trans-4-[2-(4-methylphenyl)ethyl]cyclohexylethynyl}-2,6-difluoro-4-propylbenzene;
1-{trans-4-[2-(4-ethylphenyl)ethyl]cyclohexylethynyl}-2,6-difluoro-4-propylbenzene;
1-{trans-4-[2-(4-trifluoromethylphenyl)ethyl]cyclohexylethynyl}-2,6-difluoro-4-propylbenzene;
1-{trans-4-[2-(4-difluoromethoxyphenyl)ethyl]cyclohexylethynyl}-2,6-difluoro-4-propylbenzene;
1-{trans-4-[2-(3-fluoro-4-difluoromethoxyphenyl)ethyl]cyclohexylethynyl}-2,6-difluoro-4-propylbenzene;
1-{trans-4-[2-(3,4-difluorophenyl)ethyl]cyclohexylethynyl}-2,6-difluoro-4-propylbenzene, m.p. (C/N) 62.5° C., (N/C)<28° C., cl.p. (N/I) 61.1° C.;
1-{trans-4-[2-(3-fluoro-4-chlorophenyl)ethyl]cyclohexylethynyl}-2,6-difluoro-4-propylbenzene;
1-{trans-4-[2-(3,4,5-trifluorophenyl)ethyl]cyclohexylethynyl}-2,6-difluoro-4-propylbenzene.

Example 3

Binary mixtures (BM) with 4-(trans-4-pentylcyclohexyl)benzonitrile were prepared in order to investigate the properties of the compound of formula 1 in mixtures. The threshold potential and the response times were measured at 22° C. in a TN cell (low bias tilt) having a plate separation of 8 mm; the 2.5-fold value of the threshold potential ($V_{10}$) was chosen as the operating voltage. The corresponding data for 4-(trans-4-pentylcyclohexyl)benzonitrile are: cl.p. (N/I)=54.6° C., $V_{10}$=1.62 V, $t_{on}$=22 ms, $t_{off}$=42 ms, $\Delta n$=0.120.

BM-1

90 wt. % of 4-(trans-4-pentyl-cyclohexyl)benzonitrile
10 wt. % of 1-(trans-4-propylcyclohexylethynyl)-2,6-difluoro-4-(trans-4-propylcyclohexyl)benzene;
cl.p. (N/I): 60.7° C., $V_{10}$=1.62 V, $t_{on}$=27 ms, $t_{off}$=45 ms, $\Delta n$=0.124.

BM-2

80 wt. % of 4-(trans-4-pentyl-cyclohexyl)benzonitrile
20 wt. % of 1-(trans-4-propylcyclohexylethynyl)-2,6-difluoro-4-(trans-4-propylcyclohexyl)benzene;
cl.p. (N/I): 67.6° C., $V_{10}$=1.68 V, $t_{on}$=30 ms, $t_{off}$=47 ms, $\Delta n$=0.127.

BM-3

90 wt. % of 4-(trans-4-pentyl-cyclohexyl)benzonitrile
10 wt.% of 1-(trans-4-butylcyclohexylethynyl)-2,6-difluoro-4-(trans-4-propylcyclohexyl)benzene;
cl.p. (N/I): 60.4° C., $V_{10}$=1.61 V, $t_{on}$=28 ms, $t_{off}$=45 ms, $\Delta n$=0.124.

BM-4

80 wt. % of 4-(trans-4-pentyl-cyclohexyl)benzonitrile
20 wt. % of 1-(trans-4-butylcyclohexylethynyl)-2,6-difluoro-4-(trans-4-propylcyclohexyl)benzene;
cl.p. (N/I): 67.3° C., $V_{10}$=1.68 V, $t_{on}$=32 ms, $t_{off}$=51 ms, $\Delta n$=0.125.

BM-5

90 wt. % of 4-(trans-4-pentyl-cyclohexyl)benzonitrile
10 wt. % of 1-[trans-4-(trans-4-ethylcyclohexyl)cyclohexylethynyl]-2,6-difluoro-4-propylbenzene;
cl.p. (N/I): 60.8° C., $V_{10}$=1.68 V, $t_{on}$=26 ms, $t_{off}$=45 ms, $\Delta n$=0.125.

BM-6

80 wt. % of 4-(trans-4-pentyl-cyclohexyl)benzonitrile
20 wt. % of 1-[trans-4-(trans-4-ethylcyclohexyl)cyclohexylethynyl]-2,6-difluoro-4-propylbenzene;
cl.p. (N/I): 67.3° C., $V_{10}$=1.69 V, $t_{on}$=29 ms, $t_{off}$=48 ms, $\Delta n$=0.126.

BM-7

90 wt. % of 4-(trans-4-pentyl-cyclohexyl)benzonitrile
10 wt. % of 1-{trans-4-[trans-4-(3-butenyl)cyclohexyl]cyclohexylethynyl}-2,6-difluoro-4-propyl-benzene;
cl.p. (N/I): 63.0° C., $V_{10}$=1.67 V, $t_{on}$=27 ms, $t_{off}$=45 ms, $\Delta n$=0.126.

BM-8

80 wt. % of 4-(trans-4-pentyl-cyclohexyl)benzonitrile
20 wt. % of 1-{trans-4-[trans-4-(3-butenyl)cyclohexyl]cyclohexylethynyl}-2,6-difluoro-4-propyl-benzene;
cl.p. (N/I): 72.3° C., $V_{10}$=1.79 V, $t_{on}$=27 ms, $t_{off}$=46 ms, $\Delta n$=0.130.

BM-9

90 wt. % of 4-(trans-4-pentyl-cyclohexyl)benzonitrile
10 wt. % of 1-[trans-4-(trans-4-vinylcyclohexyl)cyclohexylethynyl]-2,6-difluoro-4-ethoxybenzene;
cl.p. (N/I): 58.5° C., $V_{10}$=1.72 V, $t_{on}$=26 ms, $t_{off}$=47 ms, $\Delta n$=0.125

BM-10

80 wt. % of 4-(trans-4-pentyl-cyclohexyl)benzonitrile
20 wt. % of 1-[trans-4-(trans-4-vinylcyclohexyl)cyclohexylethynyl]-2,6-difluoro-4-ethoxybenzene;
cl.p. (N/I): 62.5° C., $V_{10}$=1.82 V, $t_{on}$=30 ms, $t_{off}$=51 ms, $\Delta n$=0.129.

BM-11

90 wt. % of 4-(trans-4-pentyl-cyclohexyl)benzonitrile
10 wt. % of 1-{trans-4-[trans-4-(2-E-chlorovinyl)cyclohexyl]cyclohexylethynyl}-2,6-difluoro-4-propylbenzene;
cl.p. (N/I): 64.6° C., $V_{10}$=1.64 V, $t_{on}$=29 ms, $t_{off}$=45 ms, $\Delta n$=0.129.

BM-12

80 wt. % of 4-(trans-4-pentyl-cyclohexyl)benzonitrile 20 wt. % of 1-{trans-4-[trans-4-(2-E-chlorovinyl)cyclohexyl]cyclohexylethynyl}-2,6-difluoro-4-propylbenzene;

cl.p. (N/I): 75.4° C., $V_{10}$=1.73 V, $t_{on}$=32 ms, $t_{off}$=51 ms, $\Delta n$=0.135.

BM-13

90 wt. % of 4-(trans-4-pentyl-cyclohexyl)benzonitrile
10 wt. % of 1-{trans-4-[trans-4-(2-E-chlorovinyl)cyclohexyl]cyclohexylethynyl}-2,6-difluoro-4-ethoxybenzene;

cl.p. (N/I): 67.3° C., $V_{10}$=1.78 V, $t_{on}$=25 ms, $t_{off}$=43 ms, $\Delta n$=0.131.

BM-14

80 wt. % of 4-(trans-4-pentyl-cyclohexyl)benzonitrile
20 wt. % of 1-{trans-4-[trans-4-(2-E-chlorovinyl)cyclohexyl]cyclohexylethynyl}-2,6-difluoro-4-ethoxybenzene;

cl.p. (N/I): 81.3° C., $V_{10}$=1.87 V, $t_{on}$=28 ms, $t_{off}$=48 ms, $\Delta n$=0.140.

BM-15

90 wt. % of 4-(trans-4-pentyl-cyclohexyl)benzonitrile
10 wt. % of 1-{trans-4-[2-(trans-4-propylcyclohexyl)ethyl]cyclohexylethynyl}-2,6-difluoro-4-propylbenzene;

cl.p. (N/I): 61.2° C., $V_{10}$=1.72 V, $t_{on}$=25 ms, $t_{off}$=42 ms, $\Delta n$=0.123.

BM-16

80 wt. % of 4-(trans-4-pentyl-cyclohexyl)benzonitrile
20 wt. % of 1-{trans-4-[2-(trans-4-propylcyclohexyl)ethyl]cyclohexylethynyl}-2,6-difluoro-4-propylbenzene;

cl.p. (N/I): 68.4° C., $V_{10}$=1.85 V, $t_{on}$=28 ms, $t_{off}$=46 ms, $\Delta n$=0.126.

BM-17

90 wt. % of 4-(trans-4-pentyl-cyclohexyl)benzonitrile
10 wt. % of 1-[trans-4-(3-fluoro-4-chlorophenyl)cyclohexylethynyl]-2,6-difluoro-4-propylbenzene;

cl.p. (N/I): 55.2° C., $V_{10}$=1.50 V, $t_{on}$=30 ms, $t_{off}$=49 ms, $\Delta n$=0.127.

BM-18

80 wt. % of 4-(trans-4-pentyl-cyclohexyl)benzonitrile
20 wt. % of 1-[trans-4-(3-fluoro-4-chlorophenyl)cyclohexylethynyl]-2,6-difluoro-4-propylbenzene;

cl.p. (N/I): 56.4° C., $V_{10}$=1.44 V, $t_{on}$=34 ms, $t_{off}$=55 ms, $\Delta n$=0.133.

BM-19

90 wt. % of 4-(trans-4-pentyl-cyclohexyl)benzonitrile
10 wt. % of 1-[trans-4-(3,4-difluorophenyl)cyclohexylethynyl]-2,6-difluoro-4-ethylbenzene;

cl.p. (N/I): 53.1° C., $V_{10}$=1.50 V, $t_{on}$=27 ms, $t_{off}$=47 ms, $\Delta n$=0.121.

BM-20

80 wt. % of 4-(trans-4-pentyl-cyclohexyl)benzonitrile
20 wt. % of 1-[trans-4-(3,4-difluorophenyl)cyclohexylethynyl]-2,6-difluoro-4-ethylbenzene;

cl.p. (N/I): 51.7° C., $V_{10}$=1.40 V, $t_{on}$=30 ms, $t_{off}$=54 ms, $\Delta n$=0.124.

BM-21

90 wt. % of 4-(trans-4-pentyl-cyclohexyl)benzonitrile
10 wt. % of 1-[trans-4-(3,4-difluorophenyl)cyclohexylethynyl]-2,6-difluoro-4-propylbenzene;

cl.p. (N/I): 53.1° C., $V_{10}$=1.49 V, $t_{on}$=29 ms, $t_{off}$=51 ms, $\Delta n$=0.123.

BM-22

80 wt. % of 4-(trans-4-pentyl-cyclohexyl)benzonitrile
20 wt. % of 1-[trans-4-(3,4-difluorophenyl)cyclohexylethynyl]-2,6-difluoro-4-propylbenzene;

cl.p. (N/I): 52.0° C., $V_{10}$=1.37 V, $t_{on}$=33 ms, $t_{off}$=54 ms, $\Delta n$=0.125.

BM-23

90 wt. % of 4-(trans-4-pentyl-cyclohexyl)benzonitrile
10 wt. % of 1-[trans-4-(3,4-difluorophenyl)cyclohexylethynyl]-2,6-difluoro-4-butylbenzene;

cl.p. (N/I): 52.3° C., $V_{10}$=1.52 V, $t_{on}$=27 ms, $t_{off}$=48 ms, $\Delta n$=0.120.

BM-24

80 wt. % of 4-(trans-4-pentyl-cyclohexyl)benzonitrile
20 wt. % of 1-[trans-4-(3,4-difluorophenyl)cyclohexylethynyl]-2,6-difluoro-4-butylbenzene;

cl.p. (N/I): 50.5° C., $V_{10}$=1.40 V, $t_{on}$=33 ms, $t_{off}$=57 ms, $\Delta n$=0.123.

BM-25

90 wt. % of 4-(trans-4-pentyl-cyclohexyl)benzonitrile
10 wt. % of 1-[trans-4-(3,4,5-trifluorophenyl)cyclohexylethynyl]-2,6-difluoro-4-ethylbenzene;

cl.p. (N/I): 51.2° C., $V_{10}$=1.45 V, $t_{on}$=27 ms, $t_{off}$=48 ms, $\Delta n$=0.121.

BM-26

80 wt. % of 4-(trans-4-pentyl-cyclohexyl)benzonitrile
20 wt. % of 1-[trans-4-(3,4,5-trifluorophenyl)cyclohexylethynyl]-2,6-difluoro-4-ethylbenzene;

cl.p. (N/I): 47.6° C., $V_{10}$=1.30 V, $t_{on}$=31 ms, $t_{off}$=58 ms, $\Delta n$=0.120.

BM-27

90 wt. % of 4-(trans-4-pentyl-cyclohexyl)benzonitrile
10 wt. % of 1-[trans-4-(3,4,5-trifluorophenyl)cyclohexylethynyl]-2,6-difluoro-4-propylbenzene;

cl.p. (N/I): 51.3° C., $V_{10}$=1.40 V, $t_{on}$=31 ms, $t_{off}$=51 ms, $\Delta n$=0.122.

BM-28

80 wt. % of 4-(trans-4-pentyl-cyclohexyl)benzonitrile
20 wt. % of 1-[trans-4-(3,4,5-trifluorophenyl)cyclohexylethynyl]-2,6-difluoro-4-propylbenzene;

cl.p. (N/I): 48.0° C., $V_{10}$=1.24 V, $t_{on}$=37 ms, $t_{off}$=60 ms, $\Delta n$=0.120.

BM-29

90 wt. % of 4-(trans-4-pentyl-cyclohexyl)benzonitrile
10 wt. % of 1-[trans-4-(3,4,5-trifluorophenyl)cyclohexylethynyl]-2,6-difluoro-4-butylbenzene;

cl.p. (N/I): 50.7° C., $V_{10}$=1.44 V, $t_{on}$=29 ms, $t_{off}$=52 ms, $\Delta n$=0.120.

BM-30

80 wt. % of 4-(trans-4-pentyl-cyclohexyl)benzonitrile
20 wt. % of 1-[trans-4-(3,4,5-trifluorophenyl)cyclohexylethynyl]-2,6-difluoro-4-butylbenzene;

cl.p. (N/I): 56.8° C., $V_{10}$=1.29 V, $t_{on}$=33 ms, $t_{off}$=62 ms, $\Delta n$=0.116.

BM-31

90 wt. % of 4-(trans-4-pentyl-cyclohexyl)benzonitrile
10 wt. % of 1-[trans-4-(3,5-difluoro-4-chlorophenyl)cyclohexylethynyl]-2,6-difluoro-4-propylbenzene;
  cl.p. (N/I): 53.3° C., $V_{10}$=1.52 V, $t_{on}$=29 ms, $t_{off}$=50 ms, $\Delta n$=0.124.

BM-32

80 wt. % of 4-(trans-4-pentyl-cyclohexyl)benzonitrile
20 wt. % of 1-[trans-4-(3,5-difluoro-4-chlorophenyl)cyclohexylethynyl]-2,6-difluoro-4-propylbenzene;
  cl.p. (N/I): 52.3° C., $V_{10}$=1.41 V, $t_{on}$=34 ms, $t_{off}$=61 ms, $\Delta n$=0.127.

BM-33

90 wt. % of 4-(trans-4-pentyl-cyclohexyl)benzonitrile
10 wt. % of 1-[trans-4-(3,5-difluoro-4-trifluoromethylphenyl)cyclohexylethynyl]-2,6-difluoro-4-propylbenzene;
  cl.p. (N/I): 50.6° C., $V_{10}$=1.43 V, $t_{on}$=29 ms, $t_{off}$=53 ms, $\Delta n$=0.121.

BM-34

80 wt. % of 4-(trans-4-pentyl-cyclohexyl)benzonitrile
20 wt. % of 1-[trans-4-(3,5-difluoro-4-trifluoromethylphenyl)cyclohexylethynyl]-2,6-difluoro-4-propylbenzene;
  cl.p. (N/I): 46.9° C., $V_{10}$1.28 V, $t_{on}$=35 ms, $t_{off}$=67 ms, $\Delta n$=0.122.

The invention has been described in terms of its preferred embodiments. Upon reading the specification, various alternative embodiments will become obvious to those skilled in the art. These embodiments are to be considered within the scope and spirit of the invention, which is only to be limited by the claims which follow and their equivalents.

What is claimed is:

1. A compound of the formula:

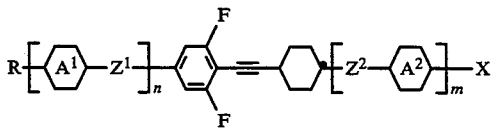

wherein
  R is an unsubstituted alkyl, alkoxy, alkenyl or alkenyloxy of 12 or less carbon atoms, or an unsubstituted alkyl, alkoxy, alkenyl or alkenyloxy of 12 or less carbon atoms in which one CH$_2$ group is replaced with oxygen, provided that no two oxygen atoms are directly adjacent, or a fluorine substituted alkyl, alkoxy, alkenyl or alkenyloxy of 12 or less carbon atoms, or a fluorine substituted alkyl, alkoxy, alkenyl or alkenyloxy of 12 or less carbon atoms in which one CH$_2$ group is replaced with oxygen, provided that no two oxygen atoms are directly adjacent;
  A$^1$ is 1,4-phenylene, or pyridine-2,5-diyl, or pyrimidine-2,5-diyl, or trans-1,4-cyclohexylene, or trans-1,3-dioxane-2,5-diyl;
  A$^2$ is trans-1,4-cyclohexylene, or unsubstituted 1,4-phenylene, or fluorine substituted 1,4-phenylene;
  Z$^1$ is a single covalent bond, —CH$_2$CH$_2$—, —OCH$_2$—, —CH$_2$O—, —(CH$_2$)$_4$—, —O(CH$_2$)$_3$—, —(CH$_2$)$_3$O— or, when ring A$^1$ is a saturated ring, the trans form of —CH=CH(CH$_2$)$_2$— or —CH=CHCH$_2$O—;
  Z$^2$ is a single covalent bond, —CH$_2$—CH$_2$—, —OCH$_2$—, —CH$_2$O—, —(CH$_2$)$_4$—, —O(CH$_2$)$_3$—, —(CH$_2$)$_3$O—, or the trans form of —CH=CH(CH$_2$)$_2$— or —CH=CHCH$_2$O—;
  n is 0 or 1;
  m is 0 or 1, provided that n+m is ≦1; and
  X is cyano, —CF$_3$, —OCF$_3$, —OCHF$_2$, —CH=CF$_2$, —CH=CHCl, or an unsubstituted alkyl, alkenyl, alkoxy, alkenyloxy or alkoxyalkyl of 6 or less carbon atoms, additionally when A$^2$ is trans-1,4-cyclohexylene, X can also be —CH=CHF or —CH=CHCl, and when A$^2$ is 1,4-phenylene, X can also be fluorine or chlorine.

2. The compound of claim 1, wherein Z$^1$ is a single covalent bond, —CH$_2$CH$_2$—, —CH$_2$O—, or —OCH$_2$—.

3. The compound of claim 2, wherein Z$^1$ is a single covalent bond or —CH$_2$CH$_2$—.

4. The compound of claim 1, wherein Z$^2$ is a single covalent bond or —CH$_2$CH$_2$—.

5. The compound of claim 1, wherein R is methyl, ethyl, propyl, butyl, pentyl, hexyl, methoxy, ethoxy, propyloxy, butyloxy, pentyloxy, hexenyloxy, 3-butenyl, 3E-pentenyl, 3E-hexenyl, 4-pentenyl, 5-hexenyl, allyloxy, 2E-butenyloxy, 3-butenyloxy, methoxymethyl, ethoxymethyl, propyloxymethyl, allyloxymethyl, methoxyethyl, ethoxyethyl, propyloxyethyl, methoxypropyl, ethoxypropyl, methoxy-1E-propenyl, or ethoxy-1E-propenyl, or when ring A$^1$ is a saturated ring also vinyl, 1E-propenyl, 1E-butenyl, 1E-pentenyl or 1E-hexenyl.

6. The compound of claim 1 having the formula:

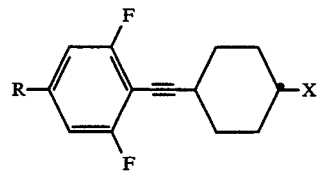

wherein
  R is an unsubstituted alkyl, alkoxy, alkenyl or alkenyloxy of 6 or less carbon atoms, or an alkyl, alkoxy, alkenyl or alkenyloxy of 6 or less carbon atoms in which one CH$_2$ group is replaced by oxygen, provided that no two oxygen atoms are directly adjacent;
  X is —OCF$_3$, —OCHF$_2$, —CH=CF$_2$, —CH=CHF, —CH=CHCl, or an unsubstituted alkyl, alkenyl, alkoxy or alkenyloxy of 3 or less carbon atoms.

7. The compound of claim 1 having the formula:

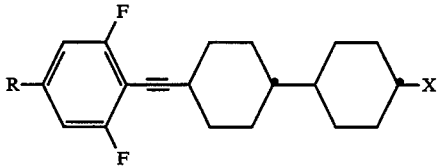

wherein
  R is an unsubstituted alkyl, alkoxy, alkenyl or alkenyloxy of 6 or less carbon atoms, or an unsubstituted alkyl, alkoxy, alkenyl or alkenyloxy of 6 or less carbon atoms in which one CH$_2$ group is replaced by oxygen, provided that no two oxygen atoms are directly adjacent; and X is —OCF$_3$, —OCHF$_2$, —CH=CF$_2$, —CH=CHF, —CH=CHCl, or an unsubstituted alkyl, alkenyl, alkoxy or alkenyloxy of 3 or less carbon atoms.

8. The compound of claim 1 having the formula:

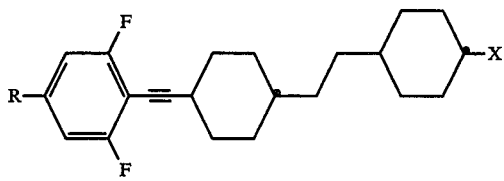

I-4 wherein

R is an unsubstituted alkyl, alkoxy, alkenyl or alkenyloxy of 6 or less carbon atoms, or an unsubstituted alkyl, alkoxy, alkenyl or alkenyloxy of 6 or less carbon atoms in which one CH$_2$ group is replaced by oxygen, provided that no two oxygen atoms are directly adjacent; and X is —OCF$_3$, —OCHF$_2$, —CH=CF$_2$, —CH=CHF, —CH=CHCl, or an unsubstituted alkyl, alkenyl, alkoxy or alkenyloxy of 3 or less carbon atoms.

9. The compound of claim 1 having the formula:

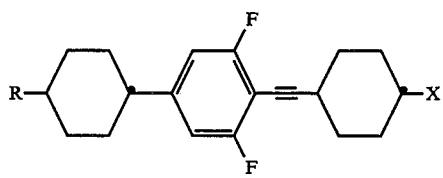

I-5 wherein

R is an unsubstituted alkyl, alkoxy, alkenyl or alkenyloxy of 6 or less carbon atoms, or an unsubstituted alkyl, alkoxy, alkenyl or alkenyloxy of 6 or less carbon atoms in which one CH$_2$ group is replaced by oxygen, provided that no two oxygen atoms are directly adjacent; and X is —OCF$_3$, —OCHF$_2$, —CH=CF$_2$, —CH=CHF, —CH=CHCl, or an unsubstituted alkyl, alkenyl, alkoxy or alkenyloxy of 3 or less carbon atoms.

10. The compound of claim 1 having the formula:

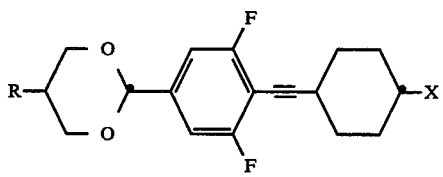

I-6 wherein

R is an unsubstituted alkyl, alkoxy, alkenyl or alkenyloxy of 6 or less carbon atoms, or an unsubstituted alkyl, alkoxy, alkenyl or alkenyloxy of 6 or less carbon atoms in which one CH$_2$ group is replaced by oxygen, provided that no two oxygen atoms are directly adjacent; and X is —OCF$_3$, —OCHF$_2$, —CH=CF$_2$, —CH=CHF, —CH=CHCl, or an unsubstituted alkyl, alkenyl, alkoxy or alkenyloxy of 3 or less carbon atoms.

11. The compound of claim 1 having the formula:

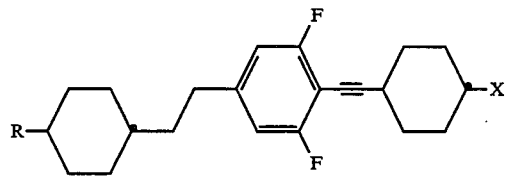

I-7 wherein

R is an unsubstituted alkyl, alkoxy, alkenyl or alkenyloxy of 6 or less carbon atoms, or an unsubstituted alkyl, alkoxy, alkenyl or alkenyloxy of 6 or less carbon atoms in which one CH$_2$ group is replaced by oxygen, provided that no two oxygen atoms are directly adjacent; and X is —OCF$_3$, —OCHF$_2$, —CH=CF$_2$, —CH=CHF, —CH=CHCl, or an unsubstituted alkyl, alkenyl, alkoxy or alkenyloxy of 3 or less carbon atoms.

12. The compound of claim 1 having the formula:

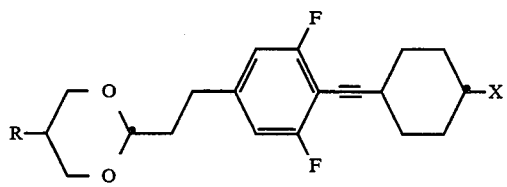

I-8 wherein

R is an unsubstituted alkyl, alkoxy, alkenyl or alkenyloxy of 6 or less carbon atoms, or an unsubstituted alkyl, alkoxy, alkenyl or alkenyloxy of 6 or less carbon atoms in which one CH$_2$ group is replaced by oxygen, provided that no two oxygen atoms are directly adjacent; and X is —OCF$_3$, —OCHF$_2$, —CH=CF$_2$, —CH=CHF, —CH=CHCl, or an unsubstituted alkyl, alkenyl, alkoxy or alkenyloxy of 3 or less carbon atoms.

13. The compound of claim 7, wherein X is a methyl, ethyl, propyl, vinyl, 1E-propenyl, —CH=CF$_2$, —CH=CHF, or —CH=CHCl.

14. The compound of claim 8, wherein X is a methyl, ethyl, propyl, vinyl, 1E-propenyl, —CH=CF$_2$, —CH=CHF, or —CH=CHCl.

15. The compound of claim 9, wherein X is a methyl, ethyl, propyl, vinyl, 1E-propenyl, —CH=CF$_2$, —CH=CHF, or —CH=CHCl.

16. The compound of claim 10, wherein X is a methyl, ethyl, propyl, vinyl, 1E-propenyl, —CH=CF$_2$, —CH=CHF, or —CH=CHCl.

17. The compound of claim 11, wherein X is a methyl, ethyl, propyl, vinyl, 1E-propenyl, —CH=CF$_2$, —CH=CHF, or —CH=CHCl.

18. The compound of claim 12, wherein X is a methyl, ethyl, propyl, vinyl, 1E-propenyl, —CH=CF$_2$, —CH=CHF, or —CH=CHCl.

19. The compound of claim 1 having the formula:

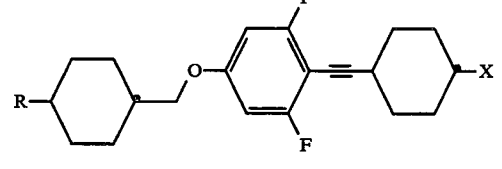

I-9 wherein

R is an unsubstituted alkyl, alkoxy, alkenyl or alkenyloxy of 6 or less carbon atoms, or an unsubstituted alkyl, alkoxy, alkenyl or alkenyloxy of 6 or less carbon atoms in which one $CH_2$ group is replaced by oxygen, provided that no two oxygen atoms are directly adjacent; and X is $-OCF_3$, $-OCHF_2$, $-CH=CF_2$, $-CH=CHF$, $-CH=CHCl$, or an unsubstituted alkyl, alkenyl, alkoxy or alkenyloxy of 3 or less carbon atoms.

20. The compound of claim 1 having the formula:

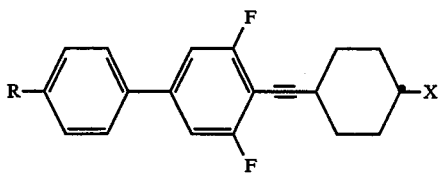

I-10 wherein

R is an unsubstituted alkyl, alkoxy, alkenyl or alkenyloxy of 6 or less carbon atoms, or an unsubstituted alkyl, alkoxy, alkenyl or alkenyloxy of 6 or less carbon atoms in which one $CH_2$ group is replaced by oxygen, provided that no two oxygen atoms are directly adjacent; and X is $-OCF_3$, $-OCHF_2$, $-CH=CF_2$, $-CH=CHF$, $-CH=CHCl$, or an unsubstituted alkyl, alkenyl, alkoxy or alkenyloxy of 3 or less carbon atoms.

21. The compound of claim 1 having the formula:

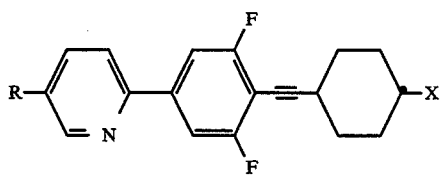

I-11 wherein

R is an unsubstituted alkyl, alkoxy, alkenyl or alkenyloxy of 6 or less carbon atoms, or an unsubstituted alkyl, alkoxy, alkenyl or alkenyloxy of 6 or less carbon atoms in which one $CH_2$ group is replaced by oxygen, provided that no two oxygen atoms are directly adjacent; and X is $-OCF_3$, $-OCHF_2$, $-CH=CF_2$, $-CH=CHF$, $-CH=CHCl$, or an unsubstituted alkyl, alkenyl, alkoxy or alkenyloxy of 3 or less carbon atoms.

22. The compound of claim 1 having the formula:

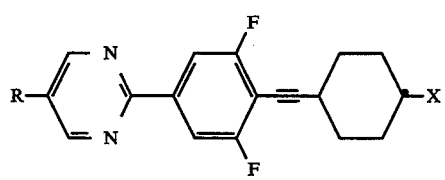

I-12 wherein

R is an unsubstituted alkyl, alkoxy, alkenyl or alkenyloxy of 6 or less carbon atoms, or an unsubstituted alkyl, alkoxy, alkenyl or alkenyloxy of 6 or less carbon atoms in which one $CH_2$ group is replaced by oxygen, provided that no two oxygen atoms are directly adjacent; and X is $-OCF_3$, $-OCHF_2$, $-CH=CF_2$, $-CH=CHF$, $-CH=CHCl$, or an unsubstituted alkyl, alkenyl, alkoxy or alkenyloxy of 3 or less carbon atoms.

23. A liquid crystalline mixture containing at least two components, wherein at least one component is:

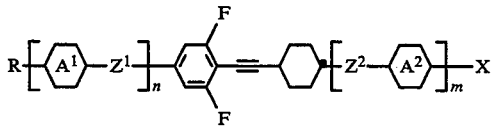

I wherein

R is an unsubstituted alkyl, alkoxy, alkenyl or alkenyloxy of 12 or less carbon atoms, or an unsubstituted alkyl, alkoxy, alkenyl or alkenyloxy of 12 or less carbon atoms in which one $CH_2$ group is replaced with oxygen, provided that no two oxygen atoms are directly adjacent, or a fluorine substituted alkyl, alkoxy, alkenyl or alkenyloxy of 12 or less carbon atoms, or a fluorine substituted alkyl, alkoxy, alkenyl or alkenyloxy of 12 or less carbon atoms in which at least one $CH_2$ group is replaced with oxygen, provided that no two oxygen atoms are directly adjacent;

$A^1$ is 1,4-phenylene, or pyridine-2,5-diyl, or pyrimidine-2,5-diyl, or trans-1,4-cyclohexylene, or trans-1,3-dioxane-2,5-diyl;

$A^2$ is trans-1,4-cyclohexylene, or unsubstituted 1,4-phenylene, or fluorine substituted 1,4-phenylene;

$Z^1$ is a single covalent bond, $-CH_2CH_2-$, $-OCH_2-$, $-CH_2O-$, $-(CH_2)_4-$, $-O(CH_2)_3-$, $-(CH_2)_3O-$ or, when ring $A^1$ is a saturated ring, the trans form of $-CH=CH(CH_2)_2-$ or $-CH=CHCH_2O-$;

$Z^2$ is a single covalent bond, $-CH_2-CH_2-$, $-OCH_2-$, $-CH_2O-$, $-(CH_2)_4-$, $-O(CH_2)_3-$, $-(CH_2)_3O-$, or the trans form of $-CH=CH(CH_2)_2-$ or $-CH=CHCH_2O-$;

n is 0 or 1;

m is 0 or 1, provided that n+m is $\leq 1$; and

X is cyano, $-CF_3$, $-OCF_3$, $-OCHF_2$, $-CH=CF_2$, $-CH=CHCl$, or an unsubstituted alkyl, alkenyl, alkoxy, alkenyloxy or alkoxyalkyl of 6 or less carbon atoms, additionally when $A^2$ is trans-1,4-cyclohexylene, X can also be $-CH=CHF$ or $-CH=CHCl$, and when $A^2$ is 1,4-phenylene, X can also be fluorine or chlorine.

24. The liquid crystalline mixture of claim 23, wherein the content of the compound of claim 1 is about 3–40 wt. %.

25. The liquid crystalline mixture of claim 24, wherein the content of the compound of claim 1 is about 5–30 wt. %.

26. A method of producing an electro-optical effect, which comprises:

(a) providing a compound of the formula

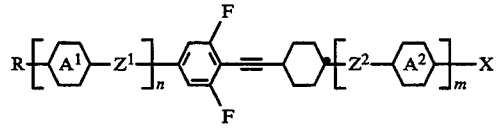

I wherein

R is an unsubstituted alkyl, alkoxy, alkenyl or alkenyloxy of 12 or less carbon atoms, or an unsubstituted alkyl, alkoxy, alkenyl or alkenyloxy of 12 or less carbon atoms in which one CH$_2$ group is replaced with oxygen, provided that no two oxygen atoms are directly adjacent, or a fluorine substituted alkyl, alkoxy, alkenyl or alkenyloxy of 12 or less carbon atoms, or a fluorine substituted alkyl, alkoxy, alkenyl or alkenyloxy group having 12 or less carbon atoms in which one CH$_2$ group is replaced with oxygen, provided that no two oxygen atoms are directly adjacent;

A$^1$ is 1,4-phenylene, or pyridine-2,5-diyl, or pyrimidine-2,5-diyl, or trans-1,4-cyclohexylene, or trans-1,3-dioxane-2,5-diyl;

A$^2$ is trans-1,4-cyclohexylene, or unsubstituted 1,4-phenylene, or fluorine substituted 1,4-phenylene;

Z$^1$ is a single covalent bond, —CH$_2$CH$_2$—, —OCH$_2$—, —CH$_2$O—, —(CH$_2$)$_4$—, —O(CH$_2$)$_3$—, —(CH$_2$)$_3$O— or, when ring A$^1$ is a saturated ring, the trans form of —CH=CH(CH$_2$)$_2$— or —CH=CHCH$_2$O—;

Z$^2$ is a single covalent bond, —CH$_2$—CH$_2$—, —OCH$_2$—, —CH$_2$O—, —(CH$_2$)$_4$—, —O(CH$_2$)$_3$—, —(CH$_2$)$_3$O—, or the trans form of —CH=CH(CH$_2$)$_2$— or —CH=CHCH$_2$O—;

n is 0 or 1;

m is 0 or 1, provided that n+m is $\leq 1$; and

X is cyano, —CF$_3$, —OCF$_3$, —OCHF$_2$, —CH=CF$_2$, —CH=CHCl, or an unsubstituted alkyl, alkenyl, alkoxy, alkenyloxy or alkoxyalkyl having 6 or less carbon atoms, additionally when A$^2$ is 1,4-cyclohexylene, X can also be —CH=CHF or —CH=CHCl, and when A$^2$ is 1,4-phenylene, X can also be fluorine or chlorine; and (b) electrically stimulating the compound to produce the desired electro-optical effect.

27. An electro-optical cell comprising:
(a) two plate means;
(b) liquid crystal means disposed between the two plate means and including a compound of the formula:

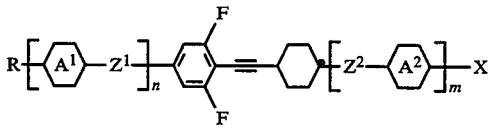

wherein

R is an unsubstituted alkyl, alkoxy, alkenyl or alkenyloxy of 12 or less carbon atoms, or an unsubstituted alkyl, alkoxy, alkenyl or alkenyloxy of 12 or less carbon atoms in which one CH$_2$ group is replaced with oxygen, provided that no two oxygen atoms are directly adjacent, or a fluorine substituted alkyl, alkoxy, alkenyl or alkenyloxy of 12 or less carbon atoms, or a fluorine substituted alkyl, alkoxy, alkenyl or alkenyloxy of 12 or less carbon atoms in which one CH$_2$ group is replaced with oxygen, provided that no two oxygen atoms are directly adjacent;

A$^1$ is 1,4-phenylene, or pyridine-2,5-diyl, or pyrimidine-2,5-diyl, or trans-1,4-cyclohexylene, or trans-1,3-dioxane-2,5-diyl;

A$^2$ is trans-1,4-cyclohexylene, or unsubstituted 1,4-phenylene, or fluorine substituted 1,4-phenylene;

Z$^1$ is a single covalent bond, —CH$_2$CH$_2$—, —OCH$_2$—, —CH$_2$O—, —(CH$_2$)$_4$—, —O(CH$_2$)$_3$—, —(CH$_2$)$_3$O— or, when ring A$^1$ is a saturated ring, the trans form of —CH=CH(CH$_2$)$_2$— or —CH=CHCH$_2$O—;

Z$^2$ is a single covalent bond, —CH$_2$—CH$_2$—, —OCH$_2$—, —CH$_2$O—, —(CH$_2$)$_4$—, —O(CH$_2$)$_3$—, —(CH$_2$)$_3$O—, or the trans form of —CH=CH(CH$_2$)$_2$— or —CH=CHCH$_2$O—;

n is 0 or 1;

m is 0 or 1, with the proviso that n+m is $\leq 1$; and

X is cyano, —CF$_3$, —OCF$_3$, —OCHF$_2$, —CH=CF$_2$, —CH=CHCl, or an unsubstituted alkyl, alkenyl, alkoxy, alkenyloxy or alkoxyalkyl of 6 or less carbon atoms, additionally when A$^2$ is trans-1,4-cyclohexylene, X can also be —CH=CHF or —CH=CHCl, and when A$^2$ is 1,4-phenylene, X can also be fluorine or chlorine; and (c) means for applying an electric potential to the plate means.

28. The compound of claim 1 having the formula:

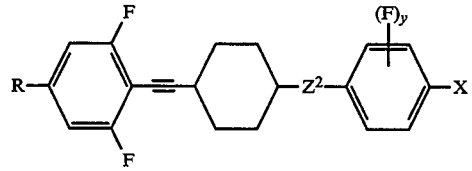

wherein

R is an unsubstituted alkyl, alkoxy, alkenyl or alkenyloxy of 6 or less carbon atoms; or an alkyl, alkoxy, alkenyl or alkenyloxy of 6 or less carbon atoms in which one CH$_2$ group is replaced by oxygen, provided that no two oxygen atoms are directly adjacent;

X is fluorine, chlorine, a cyano group, —OCHF$_2$, or —CH=CF$_2$;

Z$^2$ is a single covalent bond or —CH$_2$CH$_2$—;

Y is 0, 1 or 2, and the phenyl ring

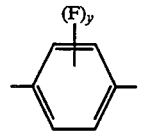

is unsubstituted or substituted as follows

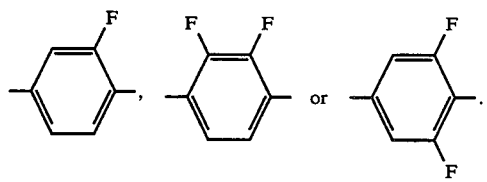

29. The compound of claim 28, wherein X is fluorine, chlorine, or cyano.

* * * * *